United States Patent
Nadeev et al.

(10) Patent No.: US 9,588,032 B2
(45) Date of Patent: *Mar. 7, 2017

(54) METHOD FOR EXAMINING SAMPLES OF FROZEN ROCKS

(71) Applicant: SCHLUMBERGER TECHNOLOGY CORPORATION, Sugar Land, TX (US)

(72) Inventors: Alexander Nikolaevich Nadeev, Spring, TX (US); Evgeny Mikhailovich Chuvilin, Moscow (RU); Olga Vladimirovna Popova, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 130 days.

This patent is subject to a terminal disclaimer.

(21) Appl. No.: 14/361,623

(22) PCT Filed: Nov. 28, 2012

(86) PCT No.: PCT/RU2012/000984
§ 371 (c)(1),
(2) Date: May 29, 2014

(87) PCT Pub. No.: WO2013/081498
PCT Pub. Date: Jun. 6, 2013

(65) Prior Publication Data
US 2014/0328449 A1 Nov. 6, 2014

(30) Foreign Application Priority Data
Nov. 29, 2011 (RU) ................................ 2011148388

(51) Int. Cl.
*G01N 1/42* (2006.01)
*G01N 1/28* (2006.01)
(Continued)

(52) U.S. Cl.
CPC ........... *G01N 15/0227* (2013.01); *G01N 1/42* (2013.01); *G01N 15/08* (2013.01); *G01N 1/28* (2013.01);
(Continued)

(58) Field of Classification Search
CPC .... A61B 6/00; A61B 6/02; A61B 6/03; A61B 6/032; A61B 6/48; A61B 6/481;
(Continued)

(56) References Cited

U.S. PATENT DOCUMENTS 3,941,191 A  3/1976  Pusch
4,587,857 A  5/1986  Bush
(Continued)

FOREIGN PATENT DOCUMENTS

RU  2316754 C1  2/2008

OTHER PUBLICATIONS

Bruker, "Cooling Stage", Retrieved on Mar. 28, 2016, http://www.skyscan.be/products/stages.htm, 2 pages.
(Continued)

*Primary Examiner* — Anastasia Midkiff

(57) ABSTRACT

A sample of frozen rocks is placed into contact with a frozen solution of an X-ray contrast agent at subzero temperature. Upon the end of saturation of the sample, a computed X-ray microtomography of the sample is conducted at a subzero temperature. The obtained microtomographic image is analyzed and spatial distribution and concentration of ice and/or gas hydrate inclusions, as well as open and closed porosity are determined.

11 Claims, 4 Drawing Sheets a b

(51) Int. Cl.
  *G01N 15/08*    (2006.01)
  *G01N 15/02*    (2006.01)
  *G01N 23/04*    (2006.01)
  *G01N 1/10*     (2006.01)
  *G01N 33/24*    (2006.01)

(52) U.S. Cl.
  CPC ......... *G01N 15/088* (2013.01); *G01N 23/046* (2013.01); *G01N 33/241* (2013.01); *G01N 2001/1068* (2013.01); *G01N 2015/0833* (2013.01); *G01N 2015/0846* (2013.01); *G01N 2223/419* (2013.01)

(58) Field of Classification Search
  CPC . A61B 6/488; G01N 1/00; G01N 1/28; G01N 1/42; G01N 2001/1062; G01N 2001/1068; G01N 2001/1081; G01N 15/00; G01N 15/02; G01N 15/0205; G01N 15/0227; G01N 15/08; G01N 2015/0833; G01N 2015/0846; G01N 23/00; G01N 23/02; G01N 23/04; G01N 23/046; G01N 23/06; G01N 23/08; G01N 23/083; G01T 1/00; G01T 1/16; G01T 1/20; G01T 1/24; G01T 2/008
  See application file for complete search history.

(56) References Cited

U.S. PATENT DOCUMENTS

| | | |
|---|---|---|
| 4,649,483 A | 3/1987 | Dixon |
| 4,722,095 A | 1/1988 | Muegge et al. |
| 4,982,086 A | 1/1991 | Withjack |
| 5,027,379 A | 6/1991 | Hunt et al. |
| 5,359,194 A | 10/1994 | Moss |
| 5,469,488 A | 11/1995 | Ono |
| 2005/0010106 A1 | 1/2005 | Lang et al. |
| 2006/0068373 A1* | 3/2006 | Bose ................ G01N 1/42 435/4 |
| 2014/0334690 A1 | 11/2014 | Nadeev et al. |

OTHER PUBLICATIONS

Chuvilin, "Migration of ions of chemical elements in frozen soils and ice", Jan. 1999, Polar Record, vol. 35, Issue 192, pp. 59-66.

Kneafsey, et al., "Examination of core samples from the Mount Elbert Gas Hydrate Stratigraphic Test Well, Alaska North Slope: Effects of retrieval and preservation", 2011, Marine and Petroleum Geology, vol. 28, No. 2, pp. 381-393.

Torrance, et al., "X-ray computed tomography of frozen soil", Jun. 2008, Cold Regions Science and Technology, vol. 53, Issue 1, pp. 75-82.

Torsaeter, et al., "The Effect of Freezing of Slightly Consolidated Cores", Sep. 1987, SPE Paper 14300-PA, pp. 357-360.

\* cited by examiner a     b

METHOD FOR EXAMINING SAMPLES OF FROZEN ROCKS

The disclosure relates to studying frozen rocks samples and can be used for investigating spatial distribution and concentration of ice and/or gas hydrate inclusions in pore space of the samples, determining size of inclusions, open or closed porosity, etc.

X-ray microtomography which makes it possible to obtain three-dimensional images of internal structure of rock samples and having resolution from 1 μm/voxel and more is widely used for non-destructive inspection of internal characteristics of a material and is used in medicine for functional diagnostics. Recently, X-ray microtomography also finds application for determining properties of rock samples in the oil and gas industry.

The method of X-ray microtomography is based on reconstruction of spatial distribution of linear attenuation coefficient (LAC) in thin layers of the sample under study with the use of computer processing of X-ray projections in different directions along the layer under study.

The value of LAC (μ) in each material depends on chemical composition, density of the material, and radiation energy $$\mu = \mu_m \rho,$$

where $\mu_m$ is a mass attenuation coefficient under the action of X-rays (cm$^2$/g), $\rho$ is a density (g/cm$^3$).

Utilization of X-ray microtomography for studying samples of frozen and hydrate-containing rocks is known from the prior art. As a rule, the method of X-ray tomography is used for study of macro ice and gas hydrate inclusions (lenses, interlayers, porphyries) and the cryohydrate texture as a whole. In particular, cryogenic structure of cores of frozen clayey formations was studied and in these studies ice laminae whose dimensions exceeded 1 mm were only seen in X-ray tomographic images [Torrance J. K., Elliot T., Martin R., Heck R. J. X-ray computed tomography of frozen soil. Cold Regions Science and Technology 53, 2008, p. 75-82]. When studying hydrate-containing formations, gas hydrate interlayers and cracks were detected that were formed in the course of dissociation of gas hydrate lenses [Kneafsey T. J, Lu H., Winters W., Boswell R., Hunter R., Collett T. S. Examination of core samples from the Mount Elbert Gas Hydrate Stratigraphic Test Well, Alaska North Slope: Effects of retrieval and preservation. Marine and Petroleum Geology 28, 2011, p. 381-393].

However these studies do not make it possible to identify intra-pore ice and hydrate inclusions due to their low contrast.

The method provides visualization of ice and/or hydrate buildups in a pore space of frozen rocks by improving their contrast which allows to estimate spatial distribution and concentration of ice and gas hydrates in the pore space of rocks, as well as to estimate open and closed porosity by analyzing X-ray images.

The method comprises placing a sample of frozen rocks in contact with a frozen solution of an X-ray contrast agent at subzero temperatures. Upon saturation of the sample with ions of the contrast agent the sample is scanned by X-ray micro Computed Tomography (micro-CT) at subzero temperatures. Obtained X-ray computed tomographic image is analyzed and three-dimensional distribution and concentration of ice and/or has hydrate inclusions as well as open and closed porosity in the sample are determined The X-ray contrast agent is a water soluble composition containing a chemical element with high level of attenuation of X-ray radiation.

The chemical element with high level of attenuation of X-ray radiation is an element with high atomic weight, and the water soluble composition is a salt or an oxide.

The element with high atomic weight is a heavy metal selected from the group of elements Pb, Ba, Sr, Ra and etc.

The contact of the sample of the frozen rocks with the frozen solution of the X-ray contrast agent is carried out at temperature below ice/gas hydrates melting in a porous space of the sample, preferably at temperatures from −7° C. to −10° C.

Preliminary the sample of the frozen rocks and the frozen solution of the X-ray contrast agent can be held at temperatures below ice/gas hydrates melting in a porous space till temperature stabilization, preferably at temperatures from −7° C. to −10° C.

The X-ray micro Computed Tomography is carried out at a temperature below ice/gas hydrates melting in a porous space of the sample, preferably at a temperature from −7° C. to −10° C.

The sample can be preliminary scanned by X-ray micro Computed Tomography.

The disclosure is illustrated by the drawings where

The method is based on the effect of diffusion of ions of water-soluble compounds of elements having the capability of attenuating the X-ray radiation (for example, salts of heavy metals) through a solid phase of ice/hydrates in a pore space of rocks at low temperatures, which improves contrast during X-ray microtomography at low (subzero) temperatures of ice/hydrate.

Suitable X-ray contrast agents are water-soluble compositions containing elements with a big atomic number, for examples, salts of heavy metals (Pb, Ba, Sr, Ra, etc.). As a salt of a heavy metal, a soluble salt is selected in accordance with the table of solubility of inorganic substances in water. Such salts may be: Pb(NO$_3$)$_2$, BaCl$_2$ and others.

In one embodiment frozen 1% solution of Pb(NO$_3$)$_2$ was used as a source of lead ions for diffusion through a solid phase of ice/gas hydrate at subzero temperatures for improving X-ray contrast in the pore space of a rock.

Saturation of ice with a salt of a metal results, for example, in lowering of the temperature of the ice-water phase transition, and that in turn may result in thawing of a sample at temperatures below 0° C. (the temperature of the ice-water phase transition for distilled water at normal pressure). On the other hand, with a decrease of temperature, rate of diffusion into the sample decreases, resulting in increase of time of contact needed for saturation of the sample with ions. In the general case, temperature at contact of a sample with a frozen solution should be lower than the temperature of the ice-water or gas hydrate-water phase transition in the sample.

The prepared 1% solution of Pb(NO$_3$)$_2$ is frozen at a temperature of −15° C. to −20° C., then the frozen solution and the frozen rock sample under study are transferred into a refrigerating chamber with temperature of about −7° C. where they are kept till temperature stabilization. After that the sample is placed on the frozen solution, i.e. their direct contact is provided. The sample in contact with the frozen solution is kept under isothermal conditions (constant temperature of about −7° C.) for 7 days. During this time, diffusion saturation of the sample of the frozen rock with heavy metal ions happens. Upon end of saturation, the contact of the sample with the frozen solution is cleaned and the frozen rock sample is ready for scanning by X-ray tomograph at subzero temperatures.

The sample is studied with the use of a low-temperature add-on unit (Cooling stage, http://www.skyscan.be/products/stages.htm) on the X-ray microtomograph. The samples were scanned at a temperature of about −10° C. in order to avoid thawing of ice in the sample.

Figure 1:
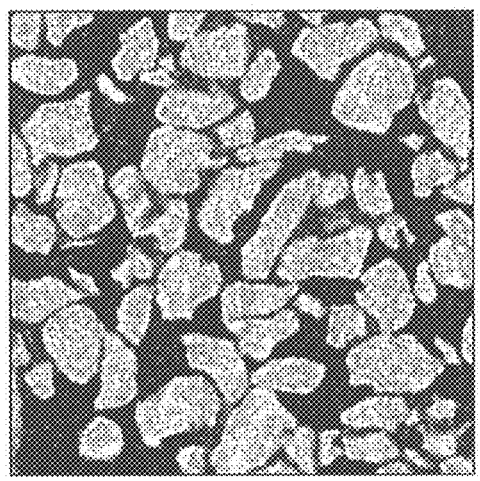
FIG. 1a shows an X-ray image obtained for a sample of frozen rocks without use of an X-ray contrast agent.
FIG. 1b shows an X-ray image obtained for a sample of frozen rocks with the use of an X-ray contrast agent.
Figure 1:
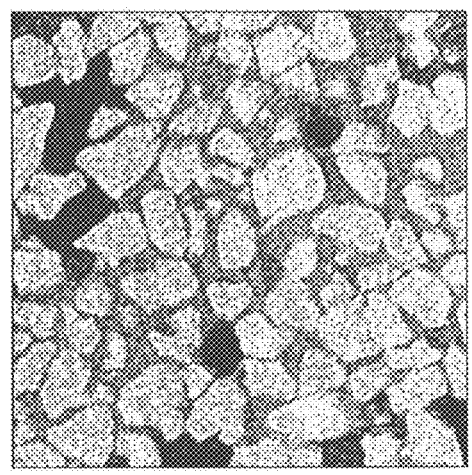
Figure 2:
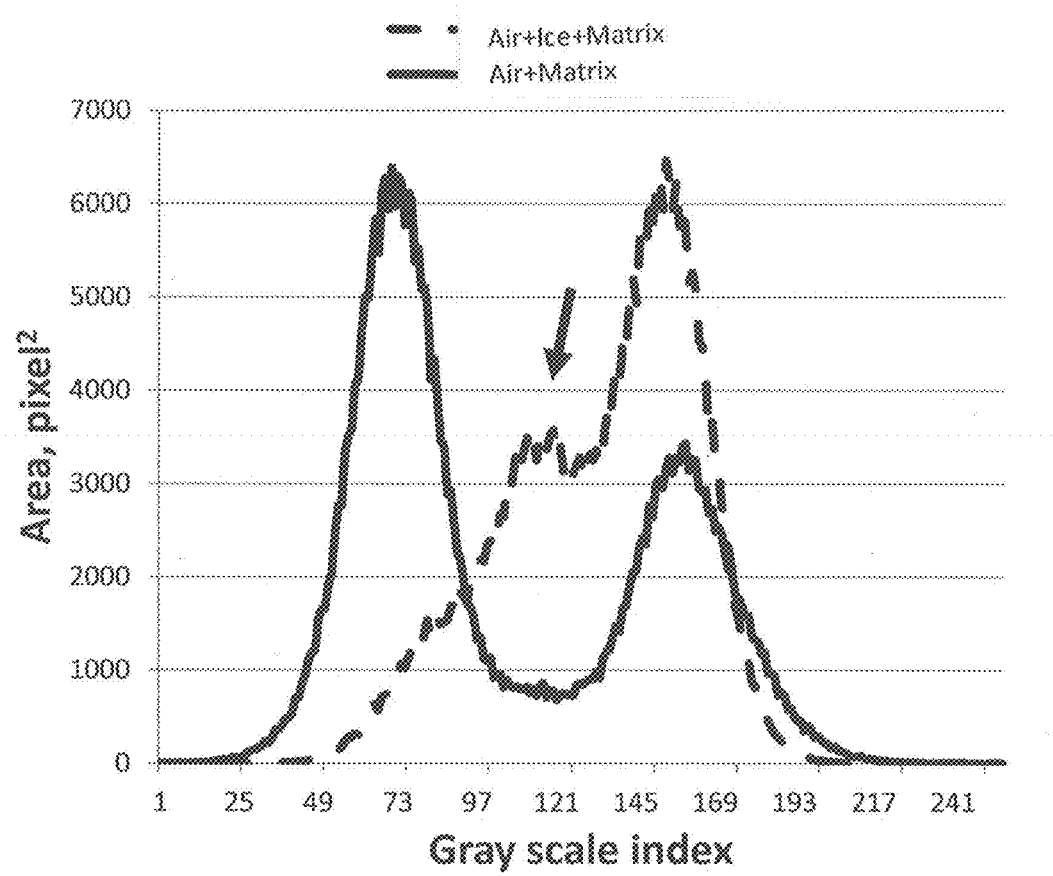
FIG. 2 shows a characteristic gray scale histogram for an ice-containing sample with and without the use of an X-ray contrast agent.
Figure 3:
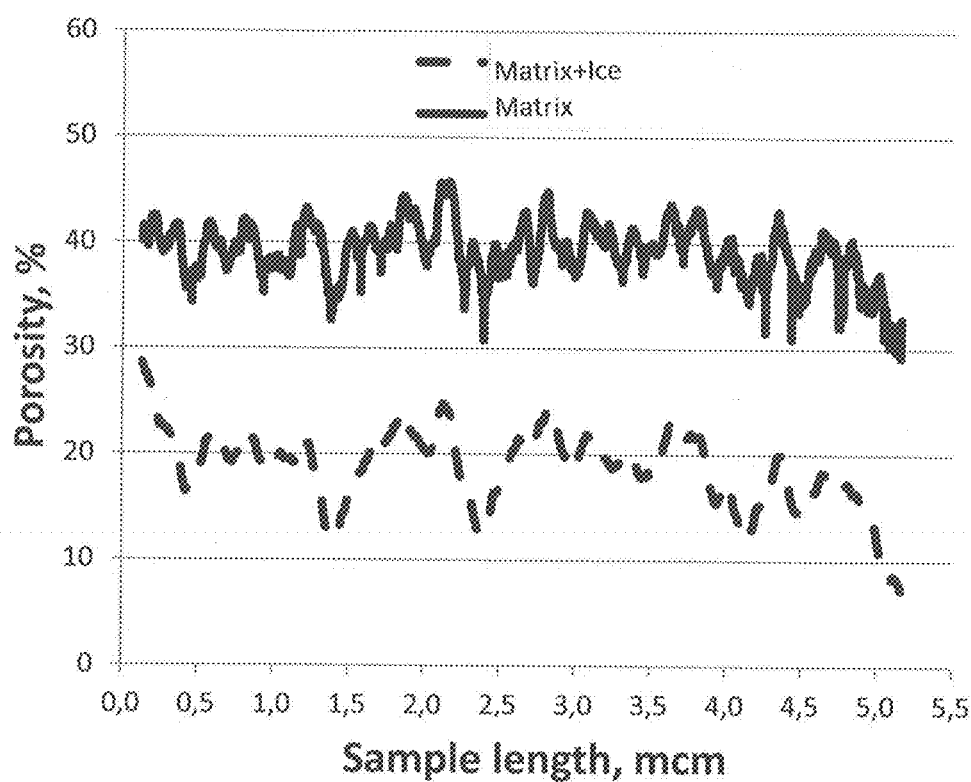
FIG. 3 shows a distribution of porosity on sample length for two cases: matrix porosity and effective porosity (with consideration of content of ice in the pores)
Figure 4:
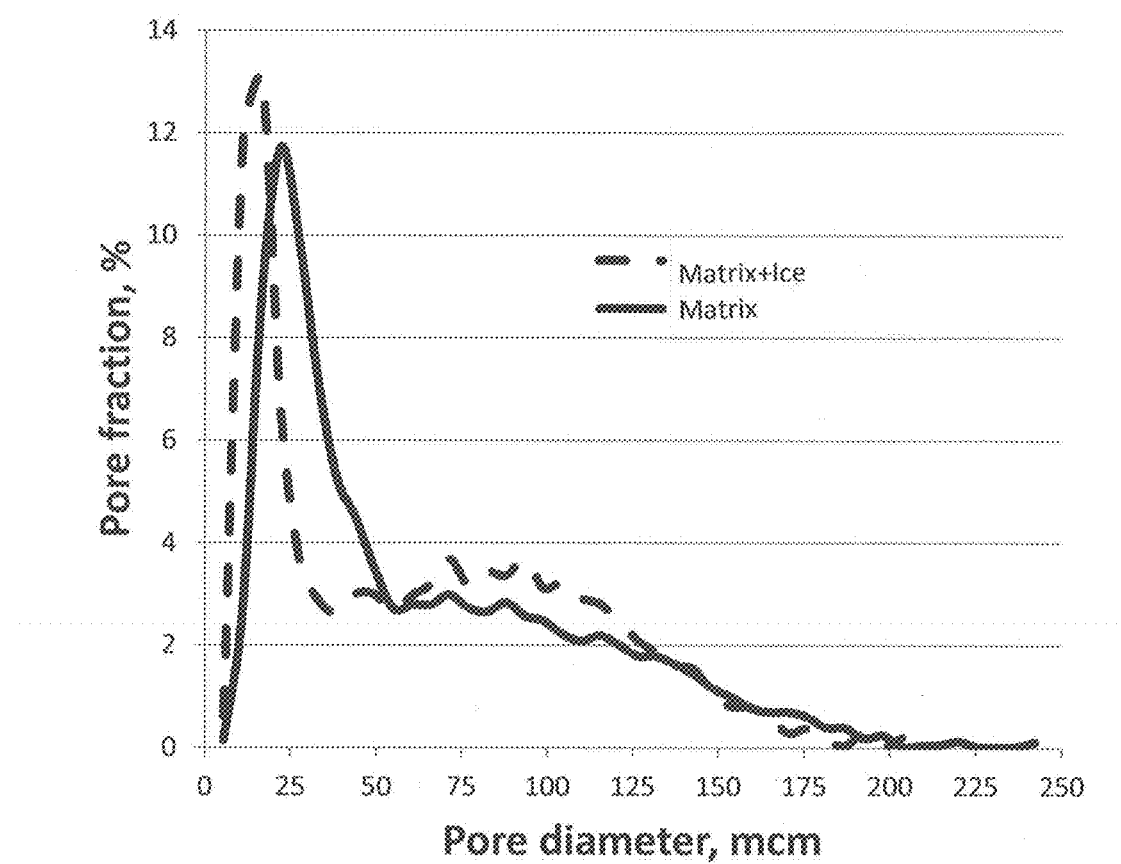
FIG. 4 shows pore size distribution for two cases: matrix porosity and effective porosity (with consideration of content of ice in the pores).

The sample should be preferably scanned with the use of an X-ray microtomograph twice, first in the original state and then after its saturation with heavy metal ions. Both scannings are to be conducted at a temperature below the temperature of melting of ice/gas hydrate in the sample. The result of scanning in both cases is a three-dimensional digital model of the core: the original one and the one after saturation with ions. In the latter, the ice/gas hydrate located in the pore space becomes visible (FIG. 1) and is displayed on the histogram of gray shades as a peak (FIG. 2, arrow). Comparative analysis of three-dimensional digital models allows determining the distribution of ice/gas hydrate in the pore space, concentration over length of the sample, pore size distribution (FIG. 3, FIG. 4), etc.

The invention claimed is:

1. A method for studying frozen rocks comprising:
providing a contact of a sample of the frozen rocks and a frozen solution of an X-ray contrast agent at subzero temperatures,
upon saturation of the sample of the frozen rocks with ions of the X-ray contrast agent scanning the sample by X-ray micro Computed Tomography at subzero temperatures,
analyzing a micro-CT image obtained by the scanning and determining three-dimensional distribution and concentration of ice and/or gas hydrates inclusions and open and closed porosity in the sample.

2. The method of claim 1, wherein the X-ray contrast agent is a water soluble composition containing a chemical element with high level of attenuation of X-ray radiation.

3. The method of claim 2, wherein the chemical element with high level of attenuation of X-ray radiation is an element with high atomic weight, and the water soluble composition is a salt or an oxide.

4. The method of claim 3, wherein the element with high atomic weight is a heavy metal selected from the group of elements Pb, Ba, Sr, Ra.

5. The method of claim 1, wherein the contact of the sample of the frozen rocks with the frozen solution of the X-ray contrast agent is carried out at temperature below ice/gas hydrates melting in a porous space of the sample.

6. The method of claim 5, wherein the contact of the sample of the frozen rocks with the frozen solution of the X-ray contrast agent is carried out at temperatures from −7° C. to −10° C.

7. The method of claim 1, wherein the sample of the frozen rocks and the frozen solution of the X-ray contrast agent are preliminary held at temperatures below ice/gas hydrates melting in a porous space till temperature stabilization.

8. The method of claim 7, wherein the sample of the frozen rocks and the frozen solution of the X-ray contrast agent are preliminary held at temperatures from −7° C. to −10° C.

9. The method of claim 1, wherein the X-ray micro Computed Tomography is carried out at a temperature below ice/gas hydrates melting in a porous space of the sample.

10. The method of claim 9, wherein the X-ray micro Computed Tomography of the sample is carried out at temperatures from −7° C. to −10° C.

11. The method of claim 9, wherein before providing the contact of the sample of the frozen rocks and the frozen solution of the X-ray contrast agent the sample is scanned by X-ray micro Computed Tomography.

* * * * *